United States Patent [19]

Allen

[11] Patent Number: 4,569,413
[45] Date of Patent: Feb. 11, 1986

[54] ENHANCED AUDIOTRANSMISSION STETHOSCOPE

[76] Inventor: Derek R. Allen, 16 Geneve, Newport Beach, Calif. 92660

[21] Appl. No.: 492,741

[22] Filed: May 9, 1983

[51] Int. Cl.$^4$ .............................................. A61B 7/02
[52] U.S. Cl. ................................................... 181/131
[58] Field of Search ............... 181/131, 137, 132, 135; 179/182 A, 182 R, 107 R, 107 E; 381/67; 73/584, 591

[56] References Cited

U.S. PATENT DOCUMENTS 3,570,625  3/1971  Allen .................................. 181/131

FOREIGN PATENT DOCUMENTS 210833  9/1908  Fed. Rep. of Germany ...... 181/131

Primary Examiner—L. T. Hix
Assistant Examiner—Brian W. Brown
Attorney, Agent, or Firm—George F. Bethel; Patience K. Bethel

[57] ABSTRACT

A stethoscope is provided which includes a stethoscope head and a pair of ear tips which are connected by tube means which provide individually separate air passages from the stethoscope head to the ear tips. The length of each of the air passages is selected such that the resonant peaks of sound transmitted from the stethoscope head to one ear lie in the resonant valleys of sound transmitted from the stethoscope head to the other ear. This is achieved by utilizing separate air passages which have a length ratio in the range of about 0.63 to about 0.73. The stethoscope is preferably utilized in conjunction with a dual stethoscope head having a bell receiver for transmitting low frequency sounds and a diaphragm receiver for transmitting high frequency sounds.

17 Claims, 16 Drawing Figures

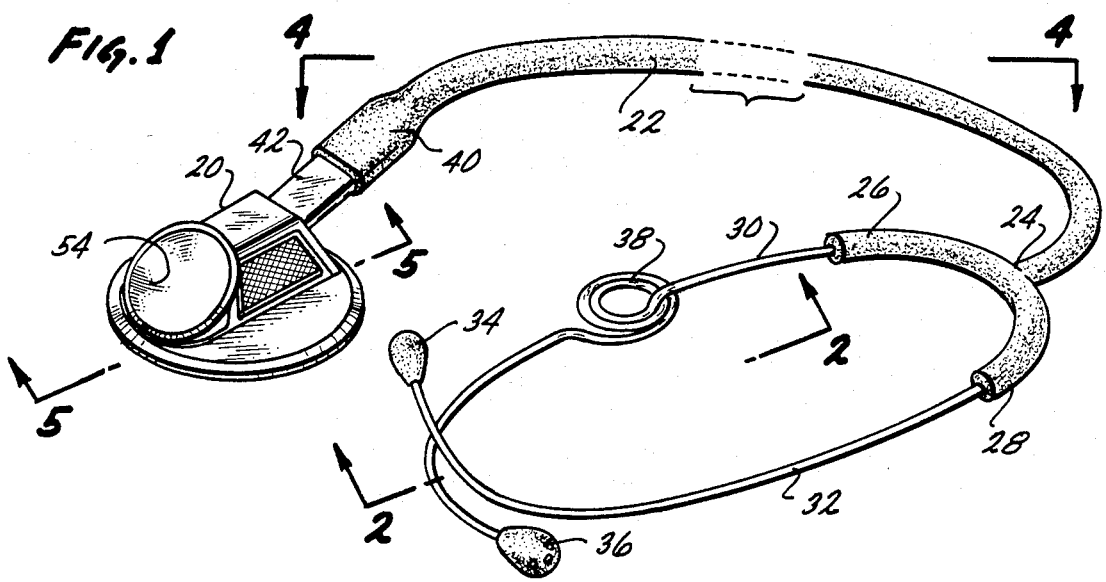
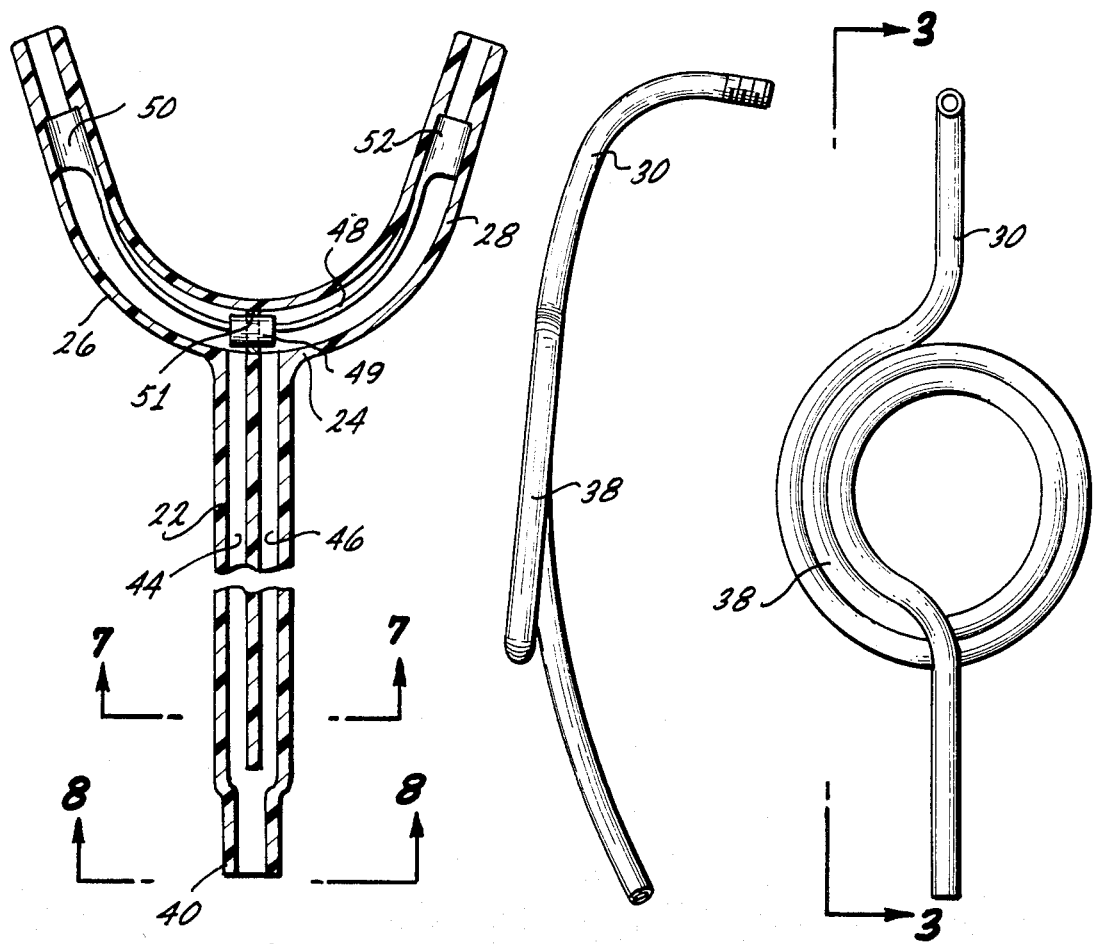

ENHANCED AUDIOTRANSMISSION STETHOSCOPE

BACKGROUND OF THE INVENTION

1. Field of the Invention

This invention relates to the field of stethoscopes, and especially to medical stethoscopes designed for auscultation. Specifically, the invention relates to stethoscopes which will be used in the audio output frequency transmission range of about fifty cycles per second to about three thousand cycles per second (Hertz).

2. The Prior Art

In my previous patent U.S. Pat. No. 3,570,625 I have disclosed and claimed a stethoscope which is comprised of a stethoscope head, a trunk tube with a common air passage and a pair of binaural tubes connected by a binaural yoke and spring. Each end of the binaural tubes terminates in an ear piece or tip. A slot within one of the binaural tubes is close to one of the ear tips and provides a means of connection and communication between the trunk tube and one of the binaural tubes through an L-junction. Thus, the trunk tube is in series with the binaural tubes leading from the first ear piece to the second ear piece. The length of the respective air columns is preferably in the ratio of one to two.

According to another preferred embodiment, the same general design of the stethoscope is maintained with the common trunk tube replaced with individually separate air columns leading from the stethoscope head to each ear piece. The theory behind this design was to create a condition through the frequency range wherein the intensity curves at the right and left air columns are complementary. That is, when the intensity curve of the air tube of the right ear begins to fall off, the intensity curve of the air tube of the left ear is rising. In actual practice, the stethoscope design was found to actually produce intensity peaks which for the most part occurred at the same place so that such peaks were not complementary. Furthermore, the stethoscope design was found to be next to impossible to manufacture because the design precluded the production of an airtight sound sealed air tube.

After considerable research, including new designs as well as sound transmission testing, I have developed a new and novel stethoscope design which is characterized by sound transmission curves wherein the resonant peaks of the air column to one ear lie substantially within the resonant valleys of the air column to the other ear. Furthermore, the design of the stethoscope is practical to manufacture and assemble, being capable of being produced in a substantially airtight sound sealed condition which minimizes distortion in the sound transmission curves. Moreover, the stethoscope design of this invention permits the monitoring of frequency ranges especially in the lower ranges which were unavailable with the prior art stethoscope designs. Furthermore, in the critical range between about eighty cycles per second to about five hundred cycles per second, there is considerable enhancement of the sound transmission permitting improved monitoring of auscultation sounds

SUMMARY OF THE INVENTION

The stethoscope of the invention comprises a stethoscope head which communicates with binaural tube means including individually separate air passages, each tube of which terminates in a pair of ear tips. Preferably, the binaural tube means comprises two separate tubes joined along a portion of its length, both of which extend from a stethoscope head. At the end opposite the jointure to the stethoscope head, the extension divides to form a yoke. A yoke spring is disposed within the yoke to urge the two separate tubes toward one another. The yoke spring passes longitudinally through and is held by a small cylinder. The cylinder is surrounded by and held in place by means of an O-ring disposed centrally within the yoke tube. The cylinder and O-ring act to divide the yoke into two individually separate air passages. Inserted into each of the ends of the yoke is a curved metal tube which terminates in an ear tip or piece. The ends of the yoke spring are crimped around the inserted ends of the metal tube to hold them securely.

One of the metal tubular extensions has a length which is substantially longer than the other extension from the yoke. Preferably, the extra length is taken up in the form of a substantially flat spiral coil such that the ear tips meet approximately at the same point for purposes of inserting into the ears of a user.

With this design the stethoscope includes separate air columns from the stethoscope head to the ear tips. The length of the air columns should be selected such that, to the extent possible, the resonant peaks of sound traveling from the stethoscope head to one ear lie in the resonant valleys of sound traveling from the stethoscope head to the other ear.

It has been found that a ratio in the range of about 0.63 to about 0.73 produces this effect. This condition permits the person utilizing the stethoscope to hear either in one ear or the other, auscultation sounds lying in the frequency range from about fifty to about one thousand cycles per second (Hertz). It is within the lower range that the rumbling murmurs can be heard and within the medium range that breathing problems can be detected. Until the present time with the stethoscope of the invention, such detection was difficult if not impossible with state of the art stethoscopes. The reason for this will be apparent in the description which follows taken in conjunction with the accompanying drawings.

DESCRIPTION OF THE DRAWINGS

The invention will be more clearly understood by reference to the description below taken in conjunction with the accompanying drawings wherein:

FIG. 1 shows a perspective view of the stethoscope of the invention;

FIG. 2 shows an enlarged view of a section of one of the air tubes as seen in the direction 2—2 of FIG. 1;

FIG. 3 shows an end view of a section of the air tube shown in FIG. 2 shown in the direction of lines 3—3 of FIG. 2;

FIG. 4 shows a section through the air tube and yoke as indicated generally at line 4—4 of FIG. 1;

DETAILED DESCRIPTION OF THE INVENTION

Figure 5:
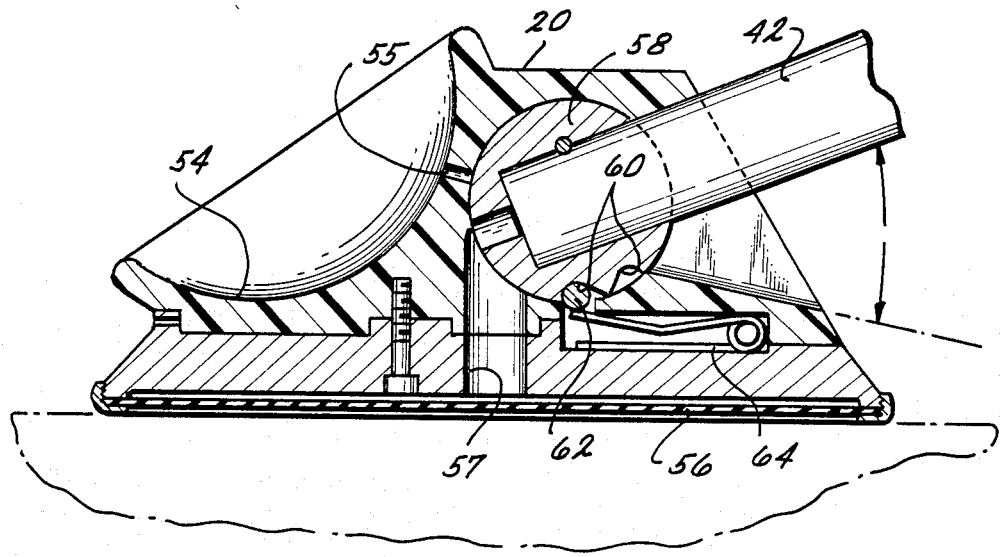
FIG. 5 shows a cross section of the stethoscope head shown in FIG. 1 taken along lines 5—5 of FIG. 1 with the air tube in sound communication with the diaphragm receiver.

Referring now to FIG. 1 there can be seen a perspective view of the stethoscope of the invention. The stethoscope includes a stethoscope head 20 which is in sound communication with an air tube 22 which terminates in a binaural yoke 24. Binaural yoke 24 has sections 26 and 28 which are in sound communication with tubing 30 and 32 respectively. Each of the tubes 30 and 32 terminate in ear pieces or tips 36 and 34 respectively. It should be noted here that tubing 30 has a length which is considerably longer than tubing 32, the difference which is taken up in a substantially flat spiral coil 38. The purpose of the coil 38 as shown in greater detail in FIGS. 2 and 3 is to absorb the extra length while at the same time avoiding sharp bends or angles which might interfere with the sound transmission through the air tube 30.

Figure 7:
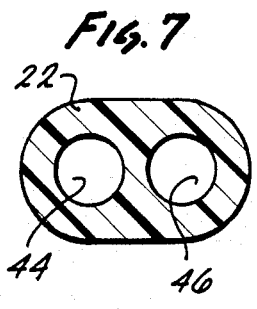
FIG. 7 shows a cross section of the sound tube of FIG. 4 taken along lines 7—7.
Figure 8:
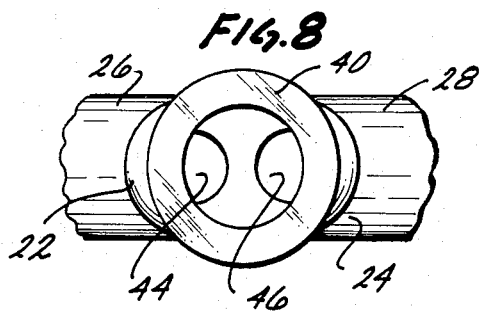
FIG. 8 shows a cross section of the air tube leading from the stethoscope head taken along lines 8—8 of FIG. 4.

The sound tube 22 and binaural yoke 24 are detailed in FIGS. 4, 7 and 8. As shown in FIG. 4 the tube 22 includes an initial section 40 of a single channel having a cross section substantially twice that of one of the binaural tubes. It is designed to friction fit over the end of sound tube 42 which projects from the stethoscope head 20. Section 40 opens into separate binaural air tubes 44 and 46 which run in a parallel direction until they meet yoke 24.

Within yoke 24 is a yoke spring 48 which is disposed longitudinally. A small cylinder 49 has a longitudinal slit therein through which the yoke spring 48 passes and is adhesively cemented thereto. The diameter of the cylinder 49 and that of the yoke spring 48 are substantially the same. An O-ring 51 which is integrally molded within the yoke 24 tightly surrounds cylinder 49 and effectively sound seals section 26 from section 28 of yoke 24. This permits sound and air to travel from air tubes 44 and 46 into sections 26 and 28 respectively. The tube 22 and sections 26 and 28 are preferably integrally formed and are preferably of a soft, smooth material, such as natural or synthetic rubber.

The purpose of the yoke spring is to urge or force the two sections 26 and 28 towards each other. Upon insertion of the metal tubing 30 and 32 it is this spring 48 which creates the clamping force which keeps the ear tips 34 and 36 within the ears.

The yoke spring 48 includes left and right flanges 50 and 52 respectively which are designed to be crimped over and hold in place the ends of metal tubing 30 and 32 upon their insertion into sections 26 and 28 of yoke 24.

Figure 6:
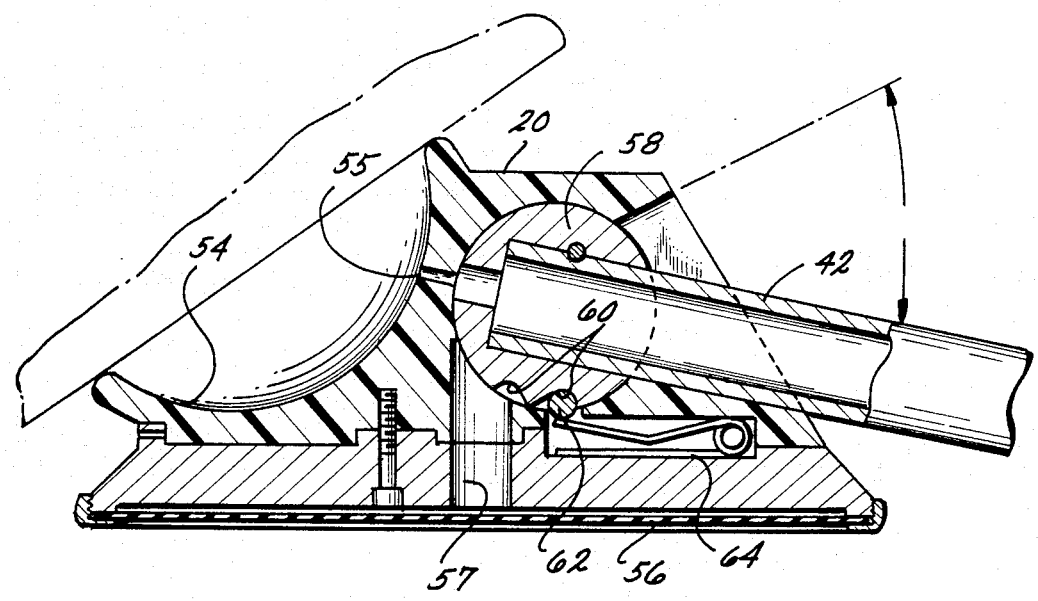
FIG. 6 shows substantially the same showing as in FIG. 5 with the exception that the air tube is positioned into sound communication with the bell receiver.

The stethoscope head 20 is detailed in FIGS. 5 and 6. This stethoscope head is the subject of my prior patent U.S. Pat. No. 4,212,368. The stethoscope head 20 includes a bell type receiver 54 and a diaphragm type receiver 56. A sound tube 42 positioned in a rotatable cylinder or valve spool 58 within the body of the stethoscope 20 can be rotated to place it in sound communication with either the bell receiver 54 through passage 55 as shown in FIG. 6 or with the diaphragm receiver 56 through passage 57 as shown in FIG. 5. The valve spool is held in place by means of a pair of grooves 60 in the outer periphery of the valve spool 58 in conjunction with a pin or bar 62 which is held in place by means of a spring 64. By such means, the sound tube 42 is easily switched from communication with the bell receiver 54 or the diaphragm receiver 56. Lower frequency sounds are received with the bell receiver 54 wherein the patient's skin acts as the diaphragm. The higher frequency sounds are received by means of the diaphragm receiver 56.

These sounds are transmitted from the bell receiver 54 or diaphragm receiver 56 through the sound tube 42 and are transmitted to the binaural tubes 44 and 46. From the binaural tubes 44 and 46 sound is transmitted through yoke 24 and sections 26 and 28 which in turn transmit the sounds through tubes 30 and 32 and finally terminate in the ear pieces 36 and 34 respectively. The sequence just described provides two individually separate air sound passages or columns from the stethoscope head 20 to the ear tips 34 and 36. Thus, sound entering tube 44 passes through section 26 through metal tube 30 through coil 38 to ear tip 36. Similarly, sound entering air tube 46 passes through section 28 through metal tube 32 to ear tip 34.

Figure 9:
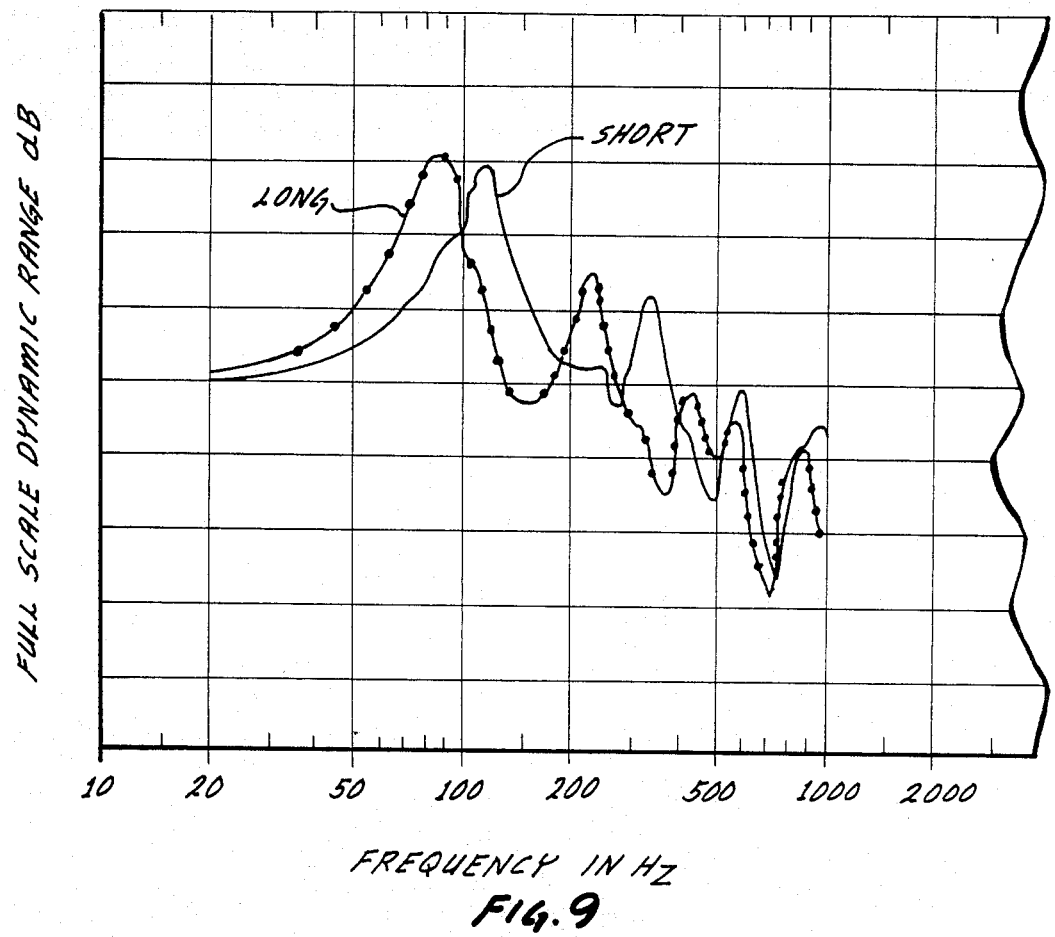
FIG. 9 shows the sound transmission curve for each of the air tubes leading from the stethoscope head to each respective ear piece; and, FIGS. 10-16 show various spiral, helix and bent-over configurations which can replace the embodiment of FIG. 2.

Each of the separate air sound passages have a characteristic sound transmission curve. These sound transmission curves are illustrated in FIG. 9. As shown, the sound transmission curve for the longer air passage which includes the metal tube 30 is shown as well as the shorter air passage corresponding to the air passage containing metal tube 32. In the monitoring of auscultation sounds, the critical range lies within the range of about 50 to about 1,000 cycles per second (Hertz).

Referring now to FIG. 9, it can be seen that if both of the sound tubes were of the same length as in prior art devices, the sound transmission curve produced by the short air passage would be the extent of what could be heard. The hearing peaks then would occur at approximately 120 Hertz, with the next peak occurring at 350 Hertz, followed by a peak at 550 Hertz, and a final peak at about 950 Hertz. If both tubes were of the same length, the sound transmission curve shown for the short tube would be all that could be heard during the monitoring of auscultation sounds.

Looking now at the sound transmission curve for the longer tube, it can be seen that there is a peak at about 90 Hertz, one at about 220 Hertz, one at about 430 Hertz, one at about 550 Hertz, and one at about 850 Hertz. In looking at the transmission curve as a whole, it is important to see that while both of the transmission curves start at the same point, the transmission curve of the longer tube rises to a peak, while the transmission curve of the short tube is still rising. Thus, as the transmission curve from the longer tube falls into a valley the shorter tube transmission curve rises to its peak. This situation is repeated along the length of the transmission curve. The result is that a greater portion of the frequency range is capable of being heard. This represents a significant improvement over prior art devices having air columns of the same length.

As mentioned previously, the relative length of the tubes should be selected such that the transmission curves complement one another. For example, the extent possible, especially within the critical range of between 50 and 1,000 Hertz (cycles per second) the relative length of the tubes should be selected to provide a condition wherein the peaks of the transmission curve of the shorter tube lie in the valleys of the transmission curve of the longer tube. It has been found that this condition is reached using air columns having a length ratio in the range of about 0.63 to about 0.73 for tubes having substantially the same inside diameters. The length ratio which is most preferred is 0.70. This is the length ratio corresponding to the sound transmission curves of FIG. 9.

FIG. 9, then, illustrates the enhanced sound transmission capabilities of the present invention. By means of the stethoscope, the low rumbling murmurs which are found in the 50 to 100 Hertz range and which are most difficult to hear are now capable of being easily detected. Similarly, areas in the medium range of between 100 at about 500 Hertz wherein breath sounds can be heard are also enhanced. The invention, thus, provides a significant improvement over prior art devices.

The tubular coiled portion 38 is such that it avoids sharp bends so as to improve the performance of the invention over the prior art. However, any coil or helix can be utilized of any geometry and orientation. The key is to have an extended tube length without sharp bends. For instance, a tube turned back on itself or any other coil or extended passage geometry which avoids sharp bends can be employed to extend the effective length with an axis inside of or outside of the axis of the passage of the tube.

It is preferred that any bend or curve used in forming the desired configuration be at least as large as an arc generated by a radius which is at least as large as about twice the inner diameter of the sound tube. For example, the sound tube preferably has an inner diameter in the range of about ⅛ inch to about 5/16 inch. Therefore, in this instance, the bends should be at least as large as an arc generated by a radius of at least about ¼ inch. If sharper bends are resorted to there will be a loss of sound transmission.

Figure 10:
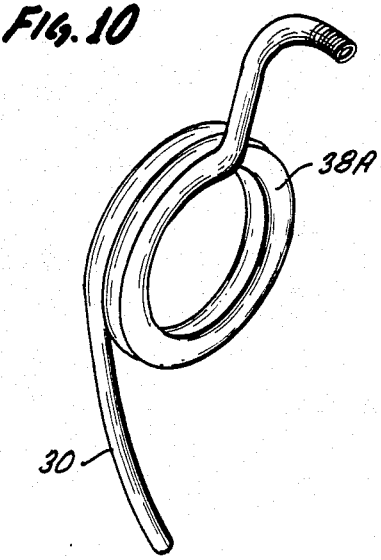
Figure 11:
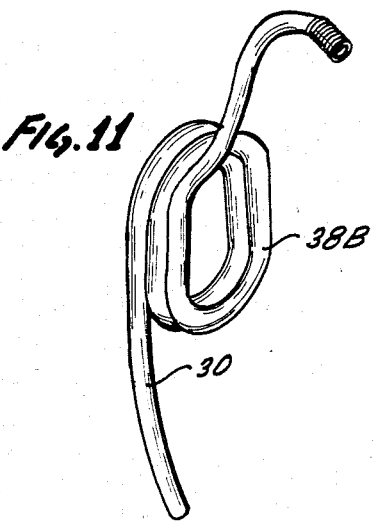
Figure 12:
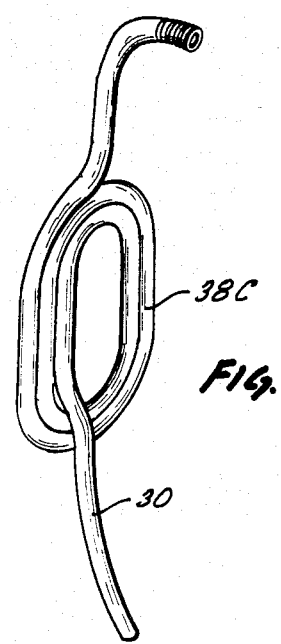
Figure 13:
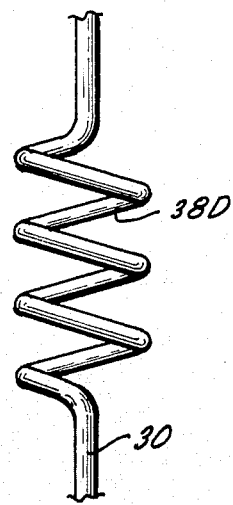
Figure 14:
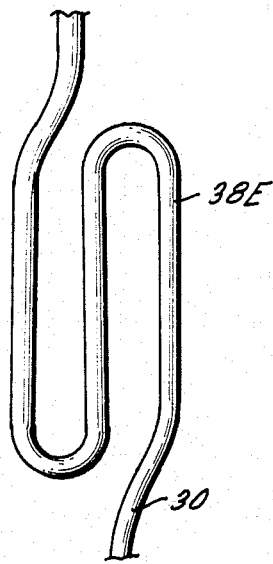
Figure 15:
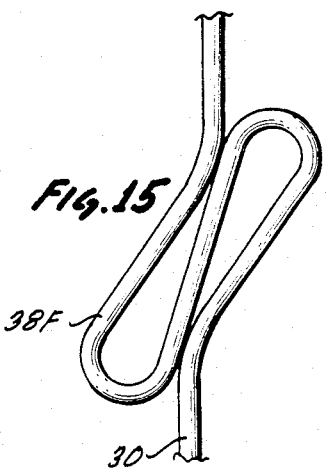
Figure 16:
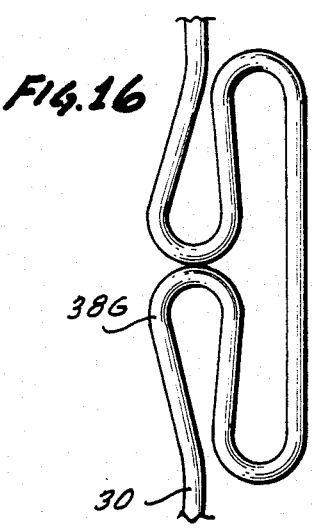

Examples of various configurations of coils or spirals can be seen in FIGS. 10–14. FIG. 10 shows a circular helix 38A; FIG. 11 shows an elongated substantially eliptical helix 38B; FIG. 12 shows a flattened eliptical helix 38C; FIG. 13 shows an elongated cylindrical helix 38D; while FIGS. 14–16, 38E, 38F and 38G show various folded-over configurations.

Having now reviewed the details of descriptions of the preferred embodiments of the invention, those skilled in the art will realize that a wide variety of structures may be employed utilizing the teachings. Many of those additional embodiments may not even resemble that depicted and described here, but such difference will not remove them from the scope of the invention as defined in the following claims.

I claim:

1. A stethoscope comprising:
a stethoscope head;
a pair of ear tips;
binaural tube means extending from said head to said ear tips and including a binaural yoke having a juncture where said binaural tube means bifurcate into two diverging channels, each channel extending to one ear tip, said tube means providing individually separate air passages of differing length from said head to said ear tips, and having a length ratio in the range of about 0.63 to about 0.73 so that the resonant peaks of sound transmission to one ear tip lie in the resonant valleys of sound transmission to the other ear tip;
wherein said binaural yoke further comprises,
a cylinder having a slit therein;
a yoke spring disposed longitudinally within said yoke, a portion of which spring passes through and is held by the slit in said cylinder; and,
a ring attached to the interior walls of said yoke and being substantially centrally disposed at the juncture of said yoke with said binaural tube means extending from said stethoscope head which ring tightly surrounds said cylinder and yoke spring to sound seal one portion of said yoke from the other at said juncture and provide a continuation of each individually separate air passage extending from said stethoscope head.

2. A stethoscope as claimed in claim 1 wherein:
said binaural tube means extending from said stethoscope head is joined along a portion of its length;
said binaural yoke is formed by a division of said joined portion of said binaural tube means into separate binaural tubes; and,
wherein said yoke spring is disposed within said yoke to urge said separate binaural tubes of said yoke together.

3. A stethoscope as claimed in claim 2 wherein:
said tube means are integrally formed.

4. A stethoscope as claimed in claim 2 wherein:
said stethoscope head includes a sound transmission tube extending therefrom; and,
wherein said binaural tube means include a section closest to said stethoscope head which is a single channel having a cross section substantially twice that of one of said binaural tubes which slip fits over the stethoscope head sound transmission tube.

5. A stethoscope as claimed in claim 2 wherein:
a portion of the longer binaural tube extending from said yoke is coiled upon itself to form a substantially flat spiral configuration, said coils using sufficient length of said tube to bring the ear tips into approximate alignment.

6. A stethoscope as claimed in claim 2 wherein:
a portion of each of said binaural tubes extending from said binaural yoke is made of a metal tube.

7. A stethoscope as claimed in claim 5 wherein:
the coiled portion of said longer binaural tube is made up of a metal tube.

8. The stethoscope as claimed in claim 1 wherein:
said individually separate air passages provided by said binaural tube means have a length ratio of about 0.70.

9. A stethoscope comprising:
a stethoscope head;
a pair of ear tips;
binaural tube means extending from said head to said ear tips providing individually separate air passages of differing length from said head to said ear tips and having a length ratio in the range of about 0.63 to about 0.73;
said binaural tube means extending from said stethoscope head being joined along a portion of its length;
a binaural yoke formed by a division of said joined portion of said binaural tube means into separate, diverging binaural tubes; and,
a yoke spring disposed within said yoke to urge said binaural tubes of said yoke together.

10. A stethoscope as claimed in claim 9 wherein:
a portion of each of said binaural tubes extending from said binaural yoke is made of a metal tube.

11. A stethoscope as claimed in claim 10 wherein:

a portion of the metal extension of said longer binaural tube is coiled upon itself to form a flat substantially spiral configuration using sufficient length to bring the ear tips into approximate alignment.

12. A stethoscope as claimed in claim 9 wherein:

said binaural tube means extending from said stethoscope head to said yoke are integrally formed.

13. A stethoscope comprising:

a stethoscope head;

a pair of ear tips;

binaural tube means extending from said head to said ear tips and including a binaural yoke having a juncture where said binaural tube means bifurcate into two diverging channels, each channel extending to one ear tip, said tube means providing individually separate air passages of differing length from said head to said ear tips and having a length ratio in the range of about 0.63 to about 0.73 so that the resonant peaks of sound transmission to one ear tip lie in the resonant valleys of sound transmission to the other ear tip; and wherein, one of said separate air passages is formed from a length of tubing having a portion turned back on itself to extend the effective length thereof;

wherein said binaural yoke further comprises:

a cylinder having a slit therein;

a yoke spring disposed longitudinally within said yoke, a portion of which spring passes through and is held by the slit in said cylinder; and, a ring attached to the interior walls of said yoke and being substantially centrally disposed at the juncture of said yoke with said binaural tube means extending from said stethoscope head which ring tightly surrounds said cylinder and contained yoke spring to sound seal one portion of said yoke from the other and provide a continuation of each individually separate air passage extending from said stethoscope head.

14. A stethoscope as claimed in claim 13 further comprising:

said tubing turned back on itself formed from a helix having an axis in line with said passage when in use.

15. A stethoscope as claimed in claim 13 further comprising:

said tubing turned back on itself having an axis at an angle to said passage when in use.

16. A stethoscope as claimed in claim 13 further comprising:

said tubing turned back on itself having an expanding helix in a relatively planar relationship to, and within the plane of said passage when in use.

17. A stethoscope as claimed in claims 11 or 13 wherein:

said length of tubing turned back on itself includes only bends which are at least as large as an arc generated by a radius which is at least as large as about twice the inner diameter of the tubing.

* * * * *